(12) United States Patent
McDonald et al.

(10) Patent No.: US 8,001,964 B2
(45) Date of Patent: Aug. 23, 2011

(54) BITE BLOCK ASSEMBLY FOR ENDOTRACHIAL TUBE

(75) Inventors: Lee McDonald, Barrie (CA); Julius Hajgato, Barrie (CA); Kenneth Noseworthy, Barrie (CA)

(73) Assignee: Southmedic Incorporated, Barrie, Ontario (CA)

( * ) Notice: Subject to any disclaimer, the term of this patent is extended or adjusted under 35 U.S.C. 154(b) by 563 days.

(21) Appl. No.: 12/241,506

(22) Filed: Sep. 30, 2008

(65) Prior Publication Data
US 2010/0078029 A1    Apr. 1, 2010

(51) Int. Cl.
*A61M 11/00*    (2006.01)
(52) U.S. Cl. ............................ 128/200.26; 128/207.14
(58) Field of Classification Search ............ 128/200.26, 128/207.14, 207.15, 207.17
See application file for complete search history.

(56) References Cited

U.S. PATENT DOCUMENTS

| | | | | |
|---|---|---|---|---|
| 5,065,755 A * | 11/1991 | Klafta | ...................... | 128/200.26 |
| D348,099 S | 6/1994 | Terrian | | |
| 5,590,643 A * | 1/1997 | Flam | ....................... | 128/200.26 |
| 5,649,534 A | 7/1997 | Briggs, III | | |
| 6,257,238 B1 * | 7/2001 | Meah | ............................. | 128/859 |
| 6,408,850 B1 * | 6/2002 | Sudge | ...................... | 128/207.17 |
| 6,517,549 B1 * | 2/2003 | Dennis | ......................... | 606/108 |
| 6,655,960 B2 * | 12/2003 | Fischer | ......................... | 433/140 |
| 7,610,912 B2 * | 11/2009 | Scopton | ................... | 128/200.26 |

OTHER PUBLICATIONS

Excerpt from website of Southmedic Incorporated, entitled *Now One Endotracheal Tube Protector Fits Multiple Sized Tubes* . . . .

* cited by examiner

*Primary Examiner* — Steven Douglas
(74) *Attorney, Agent, or Firm* — C. G. Mersereau; Nikolai & Mersereau, P.A.

(57) ABSTRACT

A bite block for an endotrachial tube includes a hollow body extending between open ends to receive an endotrachial tube such that opposing ends of the tube protrude through the open ends of the bite block. The bite block includes a tether to retain the bite block to the tube to prevent unwanted separation or movement of the tube within the bite block. The tether consists of a flexible arm which protrudes rearwardly from the bite block towards the inlet end of the tube and terminates in a ring configured to encircle the endotrachial tube, thereby effectively tethering the bite block to the tube. The arm and ring are configured such that the arm flexes in an arc when tethering the tube, thereby permitting the ring to engage the tube when fitted to thereto.

15 Claims, 5 Drawing Sheets

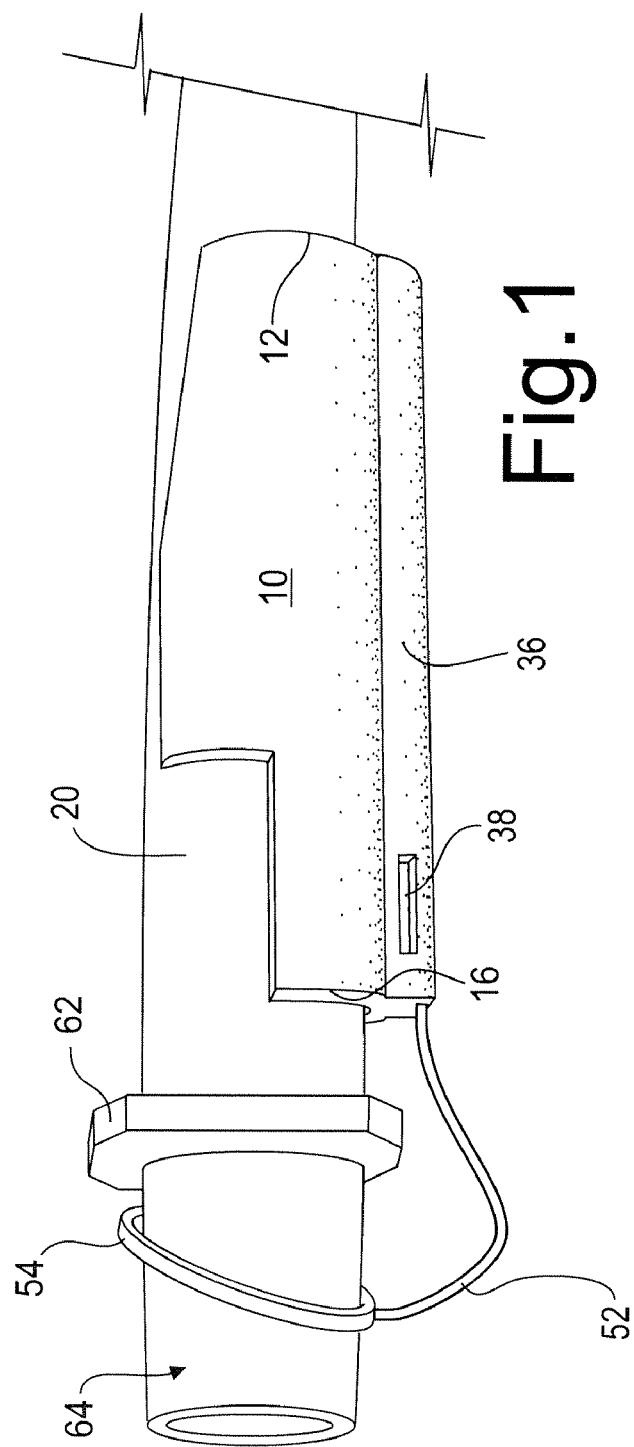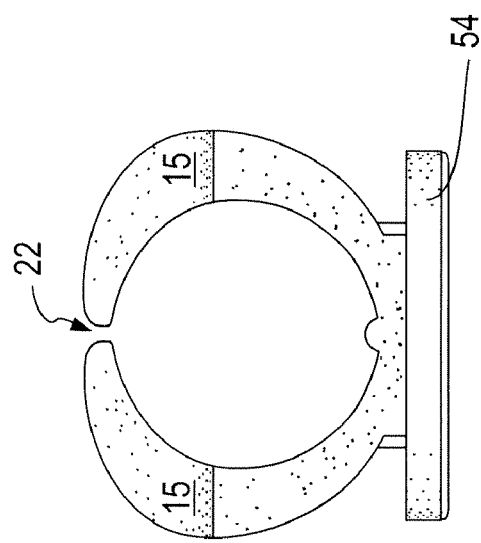

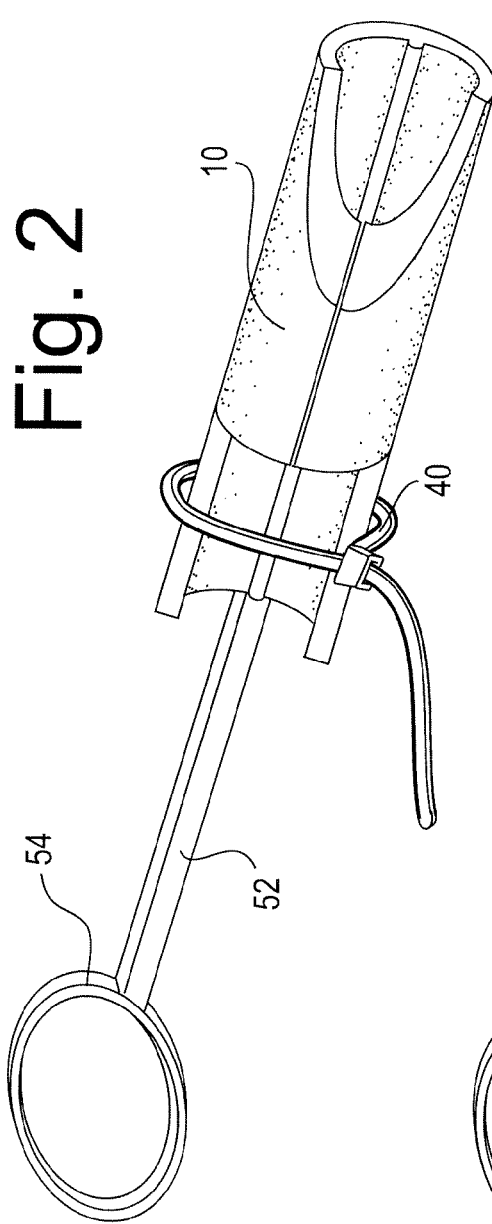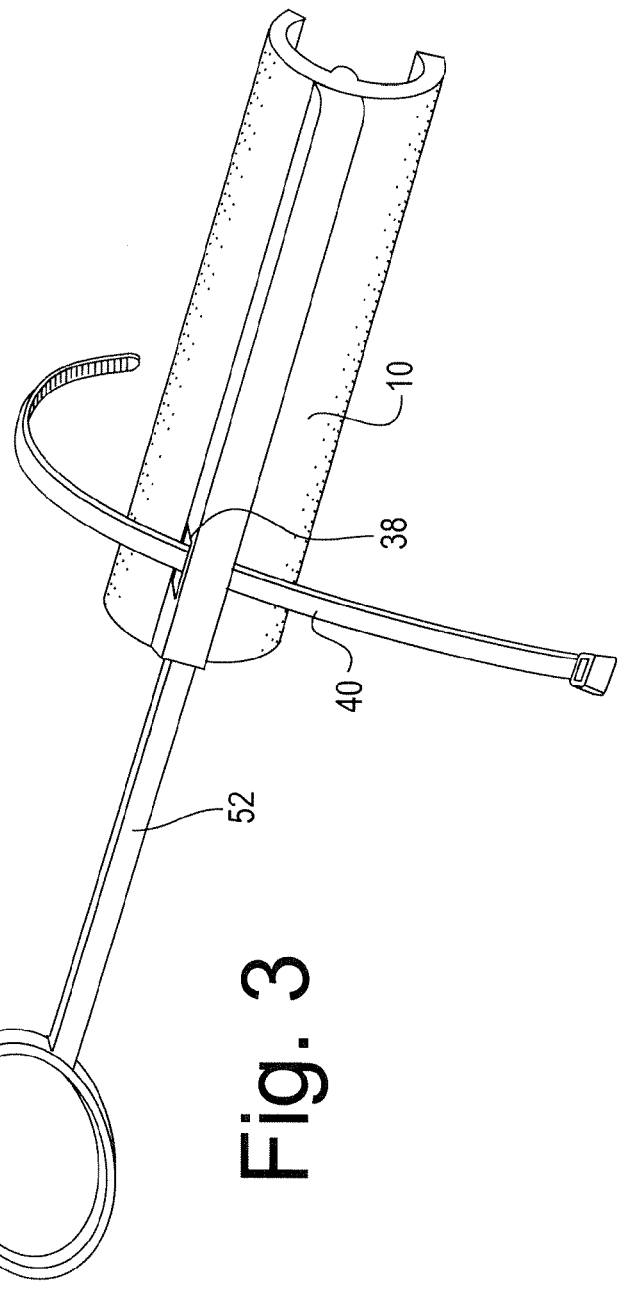

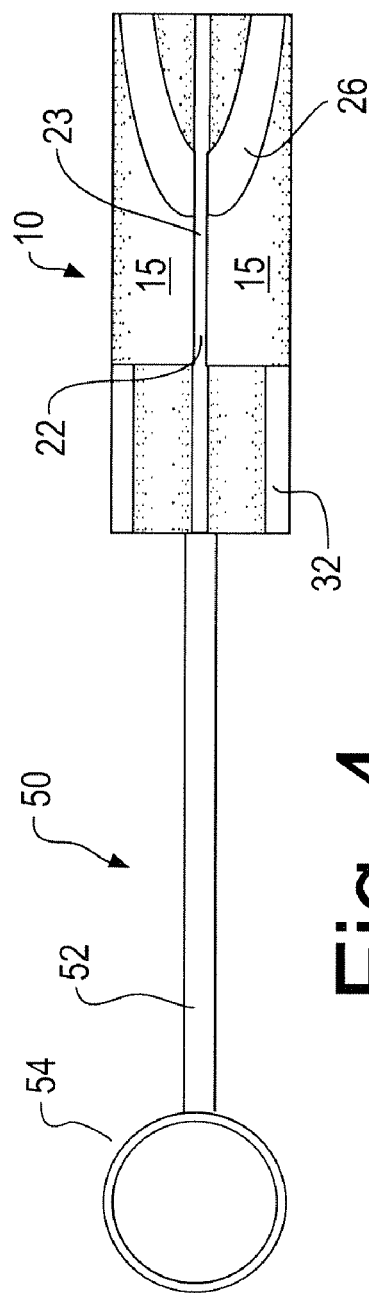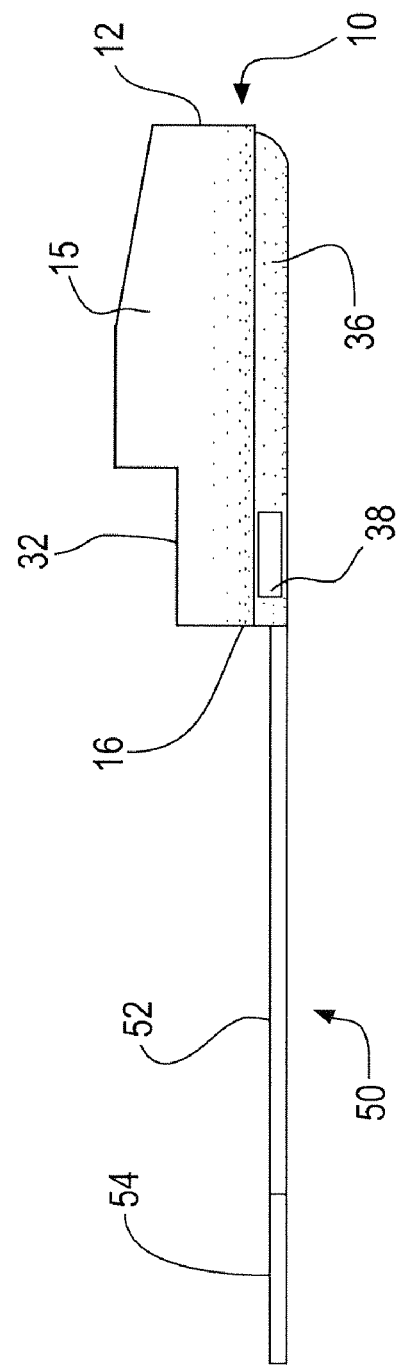

BITE BLOCK ASSEMBLY FOR ENDOTRACHIAL TUBE

FIELD OF THE INVENTION

The invention generally relates to medical devices, and more particularly to a bite block assembly for an endotracheal tube.

BACKGROUND OF THE INVENTION

Endotracheal tubes, used in various medical procedures for delivering gas to a patient, generally consist of a long tube which may be inserted into a patient's mouth and down the trachea to provide an air supply to a patient. The use of an endotracheal tube ensures that the airway is not closed off and that air is able to reach the lungs. Typically, the tube is flexible and somewhat resilient in order to easily bend through the airway of a patient and not cause tissue damage. It is often desirable to incorporate a bite block with the tube, in order to prevent a patient from biting down on the tube. The bite block consists of a relatively rigid member having a hollow interior to which encircles the tube at its upper (inlet) end where the tube enters the patient's mouth. The bite block is inserted into the patient's mouth and is retained or positioned between the patient's teeth. This is particularly useful for certain patient population groups who may have only limited control over their biting reflex. A sufficiently hard bite on a tube can pinch or even rupture the tube, thereby critically interrupting the gas flow to the patient. In response to this problem, a bite block may be provided to surround or partially surround the tube, to resist such biting. For example, bite blocks are disclosed in U.S. Pat. No. 4,896,667 (Magnussen), U.S. Pat. No. 5,649,534 (Briggs, III), and the Smedic(™) bite block sold by SouthMedic Incorporated.

When a bite block is used, it is critical that that it not become disengaged from the tube or that the tube slide within the block, since this can result in the block becoming dislodged or even in some cases sliding down a patient's trachea.

Endotracheal tubes are typically supplied in a range of sizes, and it is desirable to provide a bite block which is suitable for accommodating this range of sizes. For example, the SMedic system accommodates a range of generally conventional endotracheal tube sizes. One end of the endotrachial tube (the outlet end) is for insertion into the patients trachea, and the opposed end (the inlet end) is dimensioned for fitting a standard air supply tube.

While a typical bite block is dimensioned to accommodate even a relatively narrow endotracheal tube, slippage of the tube (especially a narrow tube) within the block can still occur. In order to prevent or reduce this, the bite block can be fastened to the tube by a tie strap. For this purpose, a tie strap may be fitted around the bite block and tube to cinch the tube and bite block together. However, especially when used with a smaller diameter endotracheal tube, it is still possible for slippage of the bite block to occur, in particular if the caregiver neglects to properly cinch the bite block to the endotrachial tube with the supplied strap, or in situations when the use of a strap is not practical. There is thus a need for an improved bite block that addresses at least some of the drawbacks within prior art devices.

Since endotracheal tubes are supplied in a range of sizes to accommodate different patient populations, some bite blocks such as the SMedic products are configured to accept a range of endotracheal tube sizes. This provides the convenience that one need only have on hand a single size of bite block, rather than a range of sizes capable of fitting a bite block. It is desirable to provide an improved bite block that securely fastens the endotracheal tube to the block while also accommodating a range of tube sizes.

SUMMARY OF THE INVENTION

According to one aspect, the invention relates to an improved bite block for an endotracheal tube. The bite block includes a body having opposed forward and rearward ends, both of which are open, and a hollow cavity extending between the ends to receive an endotrachial tube. The forward end of the body is for insertion into the mouth cavity of a patient, and the rearward end is for protruding from the patient's mouth and attachment to a gas supply tube. The bite block further comprises a tether to engage the endotracheal tube, consisting of a flexible arm protruding from the body rearwardly beyond the rearward end of the body. The arm terminates in a ring, configured to encircle the endotracheal tube so as to tether the bite block to the tube. The arm is configured to flex in an arc when the endotracheal tube is tethered to the bite block wherein the proximal end of the arm (adjacent to the bite block body) remains generally horizontal, curving towards a vertical position towards its distal end at the ring. It is preferable that the arm possesses sufficient resiliency such that the flexure of the arm about an arc imparts an angular bias to the ring when the ring is fitted over the endotrachial tube. This angular bias effectively engages the ring to the endotracheal tube by causing it to grip the tube. Preferably, the body comprises opposing inwardly curved walls that are generally C-shaped in section to define an essentially cylindrical internal cavity. The walls rise upwardly from a base and converge towards a central slot opposed to the base. The slot is defined by the spaced-apart opposed upper edges of the walls. The walls are suitably resilient to permit the user spread them outwardly with reasonable ease when an endotracheal tube is inserted into the interior of the bite block. The resiliency of the walls biases them together when a tube is engaged within the block, thereby gripping and frictionally engaging the tube.

According to one aspect, the arm and ring are substantially coplanar when the arm is unflexed, prior to assembly of the bite block to an endotracheal tube. The ring itself is planar, and is disposed on a plane parallel to the elongate axis of the body extending between the forward and rearward ends thereof. Preferable, the bite block includes a slot which extends laterally across a portion of the bite block for insertion of a tie strap for engaging the gas supply tube. The slot may be sized to fit a selected tie strap, or be sufficiently large to accommodate a range of conventional tie strap sizes.

The ring is preferably circular. However, other configurations are contemplated, such as multi-sided. The term "ring" as used herein is not limited to a circular ring, but includes and suitable configuration which serves the functions described herein.

According to another aspect, the invention relates to a combination or assembly of a bite block as described above, and an endotracheal tube dimensioned to fit into and be retained within said bite block. The endotracheal tube comprises an outlet end and an opposed inlet end for connection to a gas supply tube. The endotracheal tube may include a flange inboard from its inlet end. The combination may comprise a plurality of endotracheal tubes of varying sizes.

According to another aspect, the invention relates to a method of retaining a bite block as described herein to an endotracheal tube. The method includes the steps of:
engaging an endotracheal tube within the hollow interior of the bite block to protrude through the open ends of the bite block wherein an inlet end of said tube protrudes from said rearward end and an outlet end of said tube protrudes from said forward end;

engaging the ring to the inlet end of said endotracheal tube; and engaging the endotracheal tube to a gas supply tube.

The above steps need not be performed in the order listed above, but may be carried out in any convenient order or sequence.

In the above method, it is preferable that the ring is initially disposed on a plane parallel to the elongate axis defined the forward and rearward ends of said bite block. Normally, this is a horizontal plane when the bite block is oriented with the slot facing upwardly and the body being disposed horizontally. The endotrachial tube is inserted into the hollow interior of the bite block such that the inlet end of the tube protrudes outwardly from the bite block. The ring is fitted over the protruding inlet end of the tube. Since the ring must normally be oriented such that its opening is generally aligned with the bite block, the arm is flexed about an arc of about 90 degrees as the ring is fitted over the tube.

After being engaged to the endotrachial tube, the ring is will tend to be initially disposed on the endotracheal tube at position somewhat displaced from the end of the bite block. In this position, the ring (which is typically larger in diameter than the endotracheal tube) is disposed at a slightly non-vertical angle. This angular displacement of the ring causes it to grip the bite block, thereby loosely holding the ring in position on the tube. This permits the ring to remain in position on the endotracheal tube without the caregiver having to hold it in place before the air supply tube is engaged to the endotrachial tube/bite block assembly. According to one aspect, the air supply tube is then fastened to the endotracheal tube by sliding the two tubes together with the air supply tube overlapping the endotrachial tube. This effectively urges the ring towards the bite block, and firmly retains the ring in position close to the bite block, protruding only minimally from the bite block.

The endotrachial tube may include a flange which is inwardly displaced from its inlet end, which provides a stop for the air supply tube and wherein the ring is lodged between the flange and the outlet end of the air supply tube. The flange also prevents the bite block from moving past the patient's lips.

The invention will now be further elucidated by reference to a detailed description of certain embodiments thereof. It will be appreciated that numerous variations and departures from the particulars described herein may be made while still remaining within the scope of the invention. The full scope of the invention is defined by this patent specification as a whole, including the claims. It will also be understood the strict compliance with the description of the invention presented herein may not be necessary, and those experienced in the art will appreciate that equivalent elements may be substituted for at least some of the elements described herein. As well, any references to particular dimensions and configurations are intended merely by way of illustration and are not intended to limit the invention. Any directional references herein, such as "forward", "rearward", "horizontal" etc. are intended only for ease of description, and refer to the device in a generally horizontal position.

BRIEF DESCRIPTION OF THE DRAWINGS

FIG. 1 is a side elevational view of a bite block and endotracheal tube assembly according to the present invention.

FIG. 2 is a plan view, from above, of a bite block according to the present invention, with a retainer strap engaged thereto.

FIG. 3 is a perspective view of a bite block and retainer strap.

FIG. 4 is a plan view, from above, of the bite block.

FIG. 5 is a side elevational view of the bite block.

FIG. 6 is an end view, from the front, of a bite block of the present invention.

DETAILED DESCRIPTION

Figure 7:
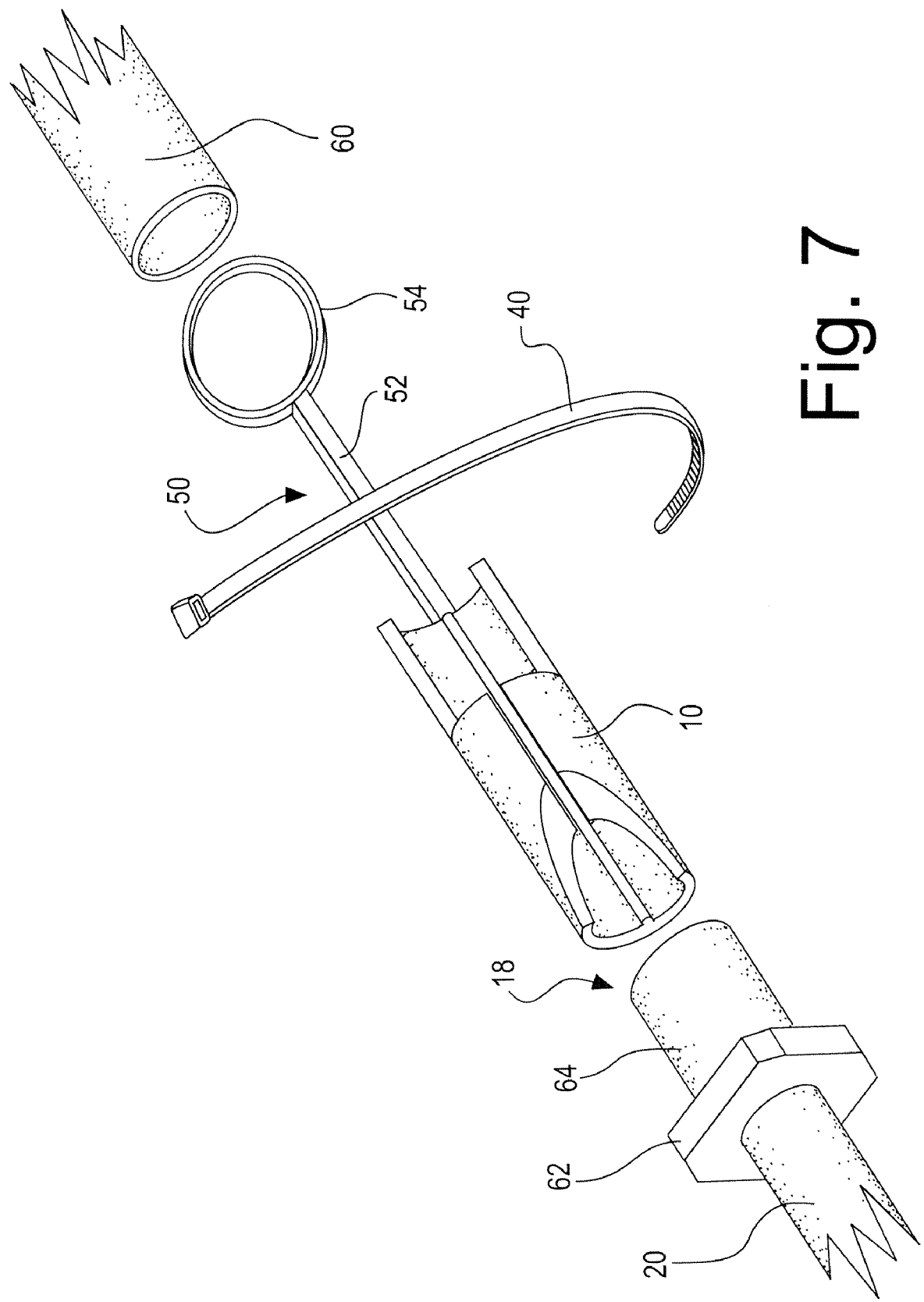
FIG. 7 is an exploded view of a bite block according to the present invention, with an endotracheal tube and tie strap.

Turning to the figures, a bite block according to the present invention consists of a generally tubular body 10, having opposed forward and rearward ends 12 and 16 respectively. When an endotracheal tube 20 is installed within the bite block, the forward end faces towards the outlet end 14 of the endotracheal tube 20 and the rearward end 16 faces the inlet end 18 of the endotracheal tube 20. When inserted into the mouth of a patient, the forward end 12 of the bite block is inserted in the patient's mouth, while the rearward end 16 protrudes outwardly from the patient's teeth. The bite block is formed from a semi-rigid molded plastic such as PVC, TPU or TPE. The material is selected to provide sufficient resiliency to permit the walls of the body to flex so as to grip an endotracheal tube, as will be described below. As well, the body 10 should have sufficient resiliency and softness to provide adequate patient comfort.

As seen more particularly in FIGS. 4, 5 and 6, the body 10 comprises a pair of opposing curved side walls 15. The side walls 15 when seen in section are generally C-shaped, and define an essentially cylindrical hollow space therebetween. At their upper edges, the walls 15 curve towards each other to define a slot 22 where their opposed upper edges face each other. The slot 22 extends lengthwise along the body 10 and communicates with the hollow interior of the body 10. The slot 22 comprises a central portion 23 where the upper edges of the walls 15 are parallel to each other and spaced closely together. At the forward end 12 of the bite block, the upper edges of the walls 15 diverge to define a V-shaped diverging slot region 26. At the opposed, rearward end of the body 10 the slot 22 defines a cutaway, downwardly stepped portion 32. The walls 15 at the stepped portion 32 define an open trough-like configuration, wherein the top edges of the sidewalls 15 are widely spaced apart, as seen in FIGS. 4, 5 and 6. This can facilitate insertion of the endotracheal tube into the interior of the body.

An elongate keel 36 extends along the lower face of the body 10 and protrudes downwardly from the body. Preferably, the keel 36 extends the full length of the body 10 so as to provide additional bite resistance. However, it is also contemplated that the keel 36 extends only partway along the body 10. A slot-like opening 38 extends through the keel in a direction transverse to the long axis of the body, adjacent to the rearward end 16 of the body 10. The opening 38 is configured to accept an optional tie strap 40 (see FIGS. 3, 7 and 8) for fastening the endotracheal tube 20 to the bite block 10, as will be described below. The opening 38 is sized to accept a range of conventional tie straps.

The bite block 10 includes a tether 50 for retaining the endotracheal tube. The tether 50 serves to prevent inadvertent separation of the bite block 10 from the endotracheal tube 20, in particular if the optional tie strap 40 is not used to fasten the tube 20 to the bite block 10. The tether 50 protrudes rearwardly from the rear of the body 10, as seen in FIGS. 4 and 5. Preferably, the tether effectively forms a rearward extension of the keel 36, and is molded together with the bite block body 10 as a single unit. The tether 50 includes an elongate arm 52 disposed along same axis as the keel 36, namely an axis which is parallel to the elongate axis of the body 10 of the bite block. The arm 52 is linear and straight when unstressed and unflexed, that is, in its relaxed position with no external force applied to flex the arm. The arm comprises a resilient material and is dimensioned to provide a relatively high degree of flexibility and resiliency, whilst still maintaining sufficient strength to resist breakage with repeated use. It is also contemplated that the arm 52 may depart from a linear configuration when unstressed and unflexed, for example it may be arcuate when in its unbiased position.

The arm terminates in a circular ring 54 which is planar (flat) when seen in side view. As seen in FIGS. 4 and 5, the long axis of the arm lies on the same plane as the ring. Preferably, the plane of the ring is horizontal when the bite block is disposed in a horizontal orientation as seen in FIG. 5. It will be seen that the ring 54 need not be precisely planar nor need it be precisely aligned with the axis of the arm 52. It is contemplated that slight departures from the configurations described herein may exist, although it is generally preferred that the ring be substantially planar and horizontal when the bite block is horizontally disposed. In this configuration, the bite block is reasonably easy to manufacture, transport, store and use.

Figure 8:
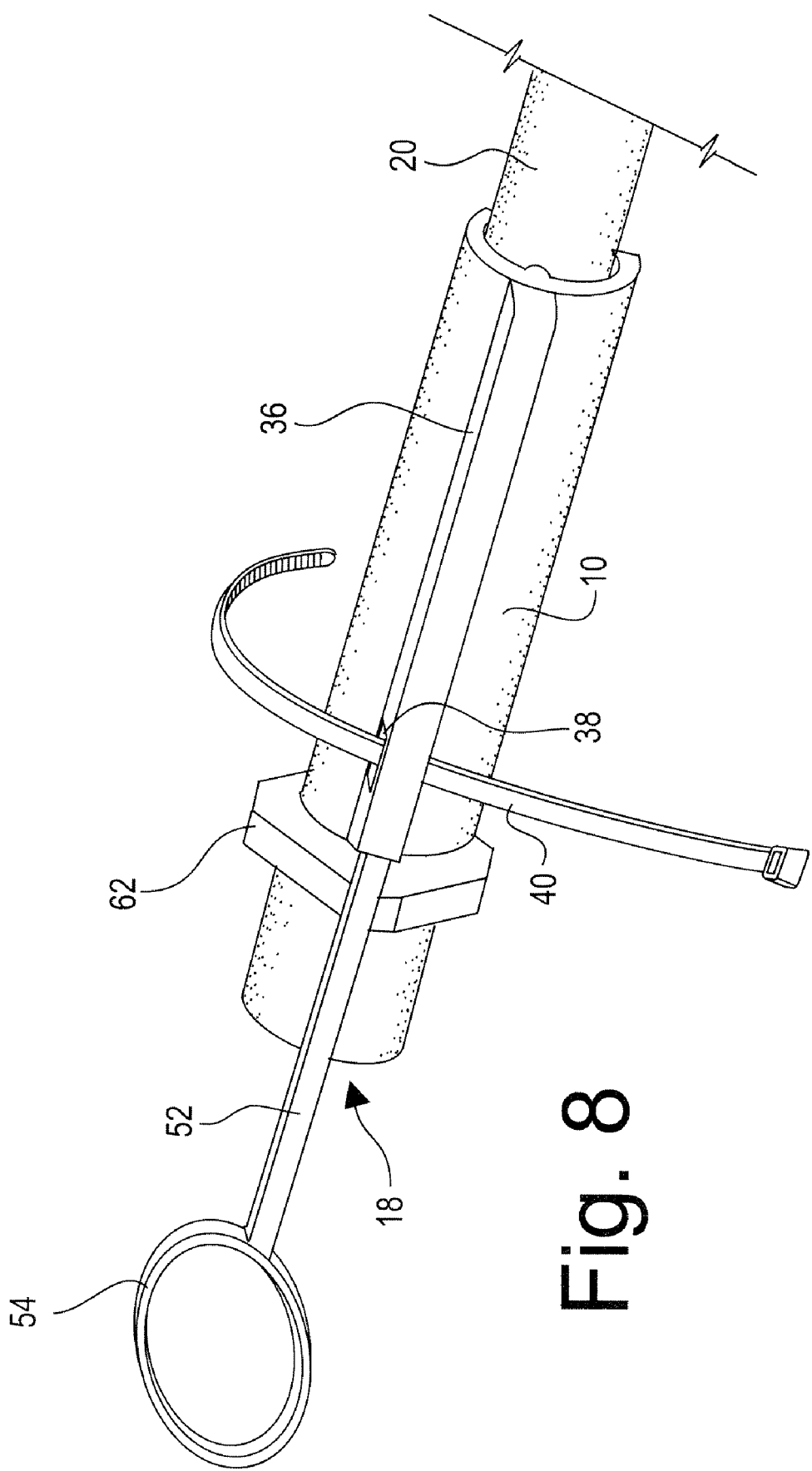
FIG. 8 is a perspective view of an assembled bite block, endotracheal tube and tie strap, prior to fastening of the gas supply tube with the endotracheal tube.

The system further comprises the endotracheal tube 20, as seen in FIGS. 1 and 7. The endotracheal tube 20 is pliable and flexible, for insertion into a patient's air passageway without causing tissue damage and/or damage to the patient's teeth. It is contemplated that the endotracheal tube 20 is generally conventional in form and configuration, and multiple such tubes may be supplied having a range of dimensions or configurations. The endotracheal tube 20 comprises an outlet end 14, for insertion into the patient's airway, and an opposed inlet end 18 for connection with an air supply tube 60 (see FIG. 7). The endotracheal tube 20 includes an outwardly protruding flange 62 adjacent to its inlet end 18, and inwardly spaced from the inlet end 18 by about 2-4 cm. The flange 62 is suitably dimensioned to abut the patient's lip region, to block movement of the bite block when retained within the patient's mouth. The endotracheal tube 20 includes an attachment section 64 consisting a length of tube at its inlet end, outboard from the flange 62, which has an outside diameter for frictionally engaging the air supply tube 60, wherein the air supply tube may be slid over the section 64. The attachment section 64 is of a size for fitting a standard air supply tube 60.

In use, the endotracheal tube 20 is clipped into the interior of the bite block 10 prior to intubation into the patient. The bite block 10 is engaged to the tube 20 at a position adjacent to and inboard (towards the outlet end 14) from the flange 62, as seen in FIG. 1. For this step, there are several ways in which the endotracheal tube 20 may inserted in the bite block. For example, the tube 20 may be initially pressed into the diverging region of the slot 26, thereby flexing the side walls 15 of the bite block 10 apart. The endotracheal tube 20 is then fully inserted into the of the interior bite block. Alternatively, the tube 20 may be threaded into the open rearward end of the bite block. The resiliency of the side walls 15 ensures a snug fit of the endotracheal tube, within a conventional range of sizes of such tubes, wherein the side walls 15 grip the tube 20 in a clamping engagement. In order to secure the bite block to the tube, the tie strap 40 is fitted through the slot, and cinched tightly around the tube. The strap 40 may be provided with the bite block 10 as part of a kit, and may consist of a generally conventional tie strap configured to fit through the slot 38 and around the bite block 10 and endotracheal tube 20. The bite block 10 may be supplied with a pre-engaged retaining strap 40, fitted within the slot 38 in an open position for fastening around the endotracheal tube when required.

It is contemplated that once the bite block 10 has been clipped to the endotracheal tube 20, the block 10 may be anchored to the tube 20 with the tether 50, and the tube 20 then engaged to an air supply tube. The caregiver may then insert the tube 20 into the patient's trachea. It is also possible to employ a different order of assembly, for example to assemble the bite block, anchor and air supply tube after insertion of the tube into the patient's trachea.

The step of anchoring the bite block 10 to the endotracheal tube 20 consists of engaging the tether 50 to the tube 20, which may be done either before or after the step of clipping the tube 20 into the interior of the bite block 10. In one approach, the assembly is initiated by fitting the ring 54 over the inlet end 18 of the tube 20, as seen in FIG. 1. In this position, the ring 54 is slid into a position adjacent to the flange 62. The arm 52 is thereby caused to flex about a curvature of approximately ninety degrees. It is also possible to slide the tube 20 into the ring 54 before the tube 20 is clipped into the bite block 10. Once the ring 54 is engaged to the tube 20, and the tube 20 is clipped into the bite block, the flexure of the arm 52 imparts an angular bias to the ring 54 acting against the engaged tube 20. Depending on the respective tube and ring diameters, the ring is more or less angled relative to the elongate axis of the tube, as seen in FIG. 1. This angular biasing retains the ring in position on the tube such that the caregiver does not have to hold onto the ring to then fasten the air supply tube 60 to the attachment section 64 of the tube 20. When the air supply tube is engaged to the endotrachial tube, the tether 50 is effectively pushed forwardly, towards the flange 62, such that the tether 50 protrudes only minimally away from the patient's face. In practice (and with practice) the ring 54 may be fitted to the endotracheal tube 20 with one hand, which can be convenient if the user's other hand is gripping the bite block.

The gas supply tube 60 is frictionally engaged to the end portion 64 of the endotracheal tube 20 by fitting the tube 60 over the end portion 64 of the endotrachial tube to ensure a gas-tight and secure fit. It is also contemplated that other attachment means between these tubes may be provided. The ring 54 is interposed between the flange 62 and the gas supply tube 60, thereby retaining the ring in position on the endotracheal tube 20. Once thus configured, the endotrachial tube and bite block assembly may be inserted into the patient's trachea (if this has not already been done) and the gas supply turned on.

Although the present invention has been described above in part by reference to detailed embodiments and other aspects, it will be understood that the full scope of the invention is not limited to the particulars described above. The full scope of the invention may be better appreciated by the present specifications and claims as a whole, including mechanical and/or structural equivalents of and to elements described herein.

The invention claimed is:

1. A bite block comprising opposed forward and rearward open ends and a hollow body extending between said open ends, said bite block being configured to receive an endotracheal tube within said hollow interior wherein an inlet end of said endotracheal tube protrudes from said rearward end and an outlet end of said tube protrudes from said forward end, said bite block further comprising a tether comprising a flexible arm protruding from said body rearwardly past said rearward end, said arm terminating in a ring configured to encircle said endotracheal tube to tether said bite block to said tube, said arm and ring being configured such that said arm is caused to flex in an arc when tethering said tube.

2. A bite block as defined in claim 1 wherein said arm is resilient so as to impart an angular bias to said ring when engaged to said tube.

3. A bite block as defined in claim 1 wherein said arm and ring are substantially co-planar when said arm is unflexed, wherein said ring is disposed on a plane generally parallel to the elongate axis of said body extending between said forward and rearward ends thereof.

4. A bite block as defined in claim 1 wherein said body includes a slot for insertion of a tie strap for engaging said endotracheal tube to said bite block.

5. A bite block as defined in claim 1 wherein said endotracheal tube includes a flange adjacent to said inlet end thereof, and said ring is configured to abut said flange when said endotracheal tube is engaged to said bite block with said tether.

6. A bite block as defined in claim 1 wherein said arc is about 90 degrees when said tether is engaged to said endotracheal tube.

7. A method of retaining a bite block to an endotracheal tube, said bite block comprising opposed forward and rearward open ends and a hollow body extending between said open ends, said bite block further comprising a tether comprising a flexible arm protruding from said body rearwardly beyond said rearward end, said arm terminating in a ring configured to encircle said endotracheal tube to tether said bite block to said tube, said arm configured to flex in an arc when tethering said tube, said method comprising carrying out the steps described below in any order or sequence:

engaging an endotracheal tube within said hollow interior to protrude through said open ends wherein an inlet end of said tube protrudes from said rearward end and an outlet end of said tube protrudes from said forward end;

engaging said ring to the inlet end of said endotracheal tube thereby flexing said arm; and engaging said endotracheal tube to a gas supply tube.

8. A method as defined in claim 7 wherein said ring is disposed on a plane parallel to the elongate axis defined the forward and rearward ends of said bite block.

9. A method as defined in claim 7 wherein said arm is resilient to impart an angular bias to said ring when flexed to engage said ring to said endotrachial tube.

10. A method as defined in claim 7 wherein said body includes a slot for insertion of a tie strap for engaging said gas supply conduit, said method further comprising supplying a tie strap, inserting said strap through said slot, and fastening said endotrachial tube to said bite block with said strap.

11. A method as defined in claim 7 wherein said endotracheal tube includes a flange adjacent to said inlet end thereof, and said ring is positioned adjacent to said flange when a gas supply tube is engaged to said endotracheal tube.

12. A method as defined in claim 7 wherein flexing of said arm causes said ring to apply an angular bias against said tube when engaged thereto, so as to retain said ring on said tube prior to connection of said tube to a gas supply conduit.

13. A bite block comprising opposed forward and rearward open ends and a hollow body extending between said open ends, said bite block being configured to receive an endotracheal tube within said hollow interior wherein an inlet end of said endotracheal tube protrudes from said rearward end and an outlet end of said tube protrudes from said forward end, said bite block further comprising a tether comprising a flexible arm protruding from said body rearwardly past said rearward end, said arm terminating in a ring configured to encircle said endotracheal tube to tether said bite block to said tube, said arm and ring being configured such that said arm is caused to flex in an arc when tethering said tube, wherein said arm is resilient so as to impart an angular bias to said ring when engaged to said tube and said arm and ring are substantially co-planar when said arm is unflexed, and wherein said ring is disposed on a plane generally parallel to the elongate axis of said body extending between said forward and rearward ends thereof.

14. A bite block assembly comprising a bite block as defined in claim 1 and at least one endotracheal tube configured to be retained within said bite block.

15. A bite block assembly comprising a bite block as defined in claim 13 and at least one endotracheal tube configured to be retained within said bite block.

\* \* \* \* \*